US008937715B2

(12) United States Patent
Fairchild et al.

(10) Patent No.: US 8,937,715 B2
(45) Date of Patent: Jan. 20, 2015

(54) OPTICAL SPECTROMETER DYNAMIC RANGE BALANCING METHODS AND APPARATUS

(71) Applicant: Kaiser Optical Systems, Ann Arbor, MI (US)

(72) Inventors: Ronald C. Fairchild, Ann Arbor, MI (US); James M. Tedesco, Livonia, MI (US); Joseph B. Slater, Dexter, MI (US)

(73) Assignee: Kaiser Optical Systems, Ann Arbor, MI (US)

( * ) Notice: Subject to any disclaimer, the term of this patent is extended or adjusted under 35 U.S.C. 154(b) by 0 days.

(21) Appl. No.: 13/903,052

(22) Filed: May 28, 2013

(65) Prior Publication Data

US 2013/0321812 A1 Dec. 5, 2013

Related U.S. Application Data

(60) Provisional application No. 61/655,112, filed on Jun. 4, 2012.

(51) Int. Cl.
| | |
|---|---|
| *G01J 3/44* | (2006.01) |
| *G01J 3/02* | (2006.01) |
| *G01N 21/65* | (2006.01) |
| *G01J 3/12* | (2006.01) |
| *G01N 21/47* | (2006.01) |

(52) U.S. Cl.
CPC ............... *G01J 3/44* (2013.01); *G01J 3/0213* (2013.01); *G01N 21/65* (2013.01); *G01J 2003/1213* (2013.01); *G01J 2003/1221* (2013.01); *G01N 2021/4742* (2013.01)

USPC ......................................................... 356/301

(58) Field of Classification Search
USPC ............................................ 356/72–73, 301
See application file for complete search history.

(56) References Cited

U.S. PATENT DOCUMENTS

| | | | |
|---|---|---|---|
| 5,247,343 A * | 9/1993 | Burch ......................... 356/451 |
| 5,786,893 A | 7/1998 | Fink et al. | |
| 6,061,134 A * | 5/2000 | Jensen et al. ................. 356/451 |
| 6,934,060 B2 | 8/2005 | Psaltis | |
| 7,532,314 B1 | 5/2009 | Black et al. | |
| 7,993,585 B2 | 8/2011 | Black et al. | |
| 8,077,309 B2 * | 12/2011 | Brown et al. ................. 356/301 |
| 2008/0212079 A1 | 9/2008 | Voigt et al. | |
| 2010/0290042 A1* | 11/2010 | Vakhshoori et al. ......... 356/301 |

* cited by examiner

*Primary Examiner* — Abdullahi Nur
(74) *Attorney, Agent, or Firm* — Gifford, Krass, Sprinkle, Anderson & Citkowski, P.C.

(57) ABSTRACT

Methods and apparatus facilitate dynamic range balancing for multi-component peaks of widely varying magnitude in an optical spectrometer. In a specific embodiment, filters attenuate the C—H stretch region to produce a better fit of a multi-component hydrocarbon Raman spectrum to the dynamic range of a CCD detector. The filter may be translated into and out of the collimated collection beam to achieve a varying degree of attenuation. In certain applications, the filter is insertable into a collimated collection beam within a fiber-optic probe head to collect Raman spectra. The invention may include optical elements to create the collimated collection beam if not already present or not suitable for insertion of the filter. A second filter, an "opaque" or neutral density filter, may be insertable into the collimated collection beam to attenuate a broad spectral response within and outside the spectral range.

12 Claims, 13 Drawing Sheets

Components

- Filter Edge Recommendations
  - Low Edge
    - High transmission: 2640 cm$^{-1}$ = 618.9 nm
    - Low transmission: 2840 cm$^{-1}$ = 626.7 nm
  - High Edge
    - Low transmission: 3070 cm$^{-1}$ = 635.8 nm
    - High transmission: 3270 cm$^{-1}$ = 644.0 nm

*Fig - 4A*

OPTICAL SPECTROMETER DYNAMIC RANGE BALANCING METHODS AND APPARATUS

REFERENCE TO RELATED APPLICATION

This application claims priority from U.S. Provisional Patent Application Ser. No. 61/655,112, filed Jun. 4, 2012, the entire content of which is incorporated herein by reference.

FIELD OF THE INVENTION

This invention relates generally to Raman spectroscopy and, in particular, to methods and apparatus for dynamic range balancing for multi-component peaks of widely varying magnitude in an optical spectrometer.

BACKGROUND OF THE INVENTION

In Raman spectroscopy, the molecular fingerprint region is in the range of 700 to 1800 $cm^{-1}$. Many different vibrations, including C—O, C—C and C—N single bond stretches, C—H bending vibrations, and some bands due to benzene rings are found in this region. However, many functional groups exhibit vibrational peaks at similar Raman shifts regardless of the structure of the rest of the molecule. For example, C—H stretching vibrations usually appear between 2800 and 3200 $cm^{-1}$ and carbonyl (C=O) stretching vibrations usually appear between 1600 and 1800 $cm^{-1}$. Raman spectra of hydrocarbon molecules tend to be dominated by strong features in the C—H stretch band. However, weaker peaks in the fingerprint region and elsewhere can be better suited to identification and quantitation of multiple components of a hydrocarbon sample stream. Practical examples of industrial applications for Raman analyzers involving hydrocarbon quantitation include natural gas transfer and synthetic fuels manufacturing.

In many hydrocarbon applications of Raman spectroscopy, the sample stream consists of many different components such as those listed in the table of FIG. 1. The different components may be present in widely varying relative concentrations, from very strong to very weak. The purpose of the analyzer is normally to measure each of those relative concentrations with as high accuracy as possible. This enables the analyzer to assist with the control of process parameters in synthetic fuels manufacturing, or to measure the energy content in a stream of natural gas. In the natural gas example, the dominant component by far is methane. Methane's primary peak for quantitation is in the C—H stretch region, where it can be an order of magnitude stronger than the next strongest features of the natural gas spectrum.

Further, many practical implementations of industrial Raman analyzers are capable of probing multiple sample streams simultaneously. This is typically done by feeding the Raman signals from each stream through individual fibers all coupled to a common spectrograph input. The spectrograph then disperses the spectrum of each sample stream onto different regions of a common CCD or other array detector camera. By the very nature of those array cameras, every detector on the array is read out with a common integration time. That integration time must be selected to be a) short enough so that the strongest signals of interest do not saturate the charge capacity of the detector or readout register, yet b) long enough so that the weakest signals of interest will rise above the electronic noise of the readout amplifier and the quantization noise of the analog-to-digital converter.

In such a multiple-sample analyzer application, the range of signal peak levels present within a given spectrum is further exacerbated by the fact that the separate spectra may be of very different overall magnitudes with respect to each other. This may be due to, for example, very different stream pressures, temperatures or compositions at the different sample points. As such, it is desirable to provide means for individually pre-conditioning each sample point spectrum upstream of the spectrograph such that a) very strong signals within a given sample spectrum, such as those within the C—H stretch region, are preferentially attenuated relative to the weak signals within that spectrum, and/or b) very strong sample point spectra are preferentially attenuated in a spectrally neutral sense with respect to the weaker sample point spectra in a multi-channel analyzer. Such means bring all spectral features of interest across all channels into better balance with the dynamic range of the array camera. This allows the inherently weaker signals to be measured with sufficient signal-to-noise ratio (SNR), while the inherently stronger signals (e.g. those in the stretch region and/or those from higher pressure sample streams) may simultaneously be measured to high SNR without saturating the camera.

FIG. 2 is an overlay of pure gas signals representing the component gasses of interest in a typical hydrocarbon application, obtained from an Optograf gas spectrum analyzer (Kaiser Analytics, Ann Arbor, Mich. 48103). As can be seen, the multi-component peaks in the C—H stretch region are significantly stronger and closer together than those of the fingerprint region. FIG. 3 is a detailed graph of the C—H stretch region.

SUMMARY OF THE INVENTION

This invention resides in methods and apparatus for dynamic range balancing for multi-component peaks of widely varying magnitude in an optical spectrometer. The preferred embodiment is directed to filters that attenuate the C—H stretch region to produce a better fit of a multi-component hydrocarbon Raman spectrum to the dynamic range of a CCD detector.

In the preferred embodiment, the filter used to attenuate the multi-component peaks of varying magnitude is translatable into and out of the collimated collection beam to achieve a varying degree of attenuation. In certain applications, the filter is insertable into a collimated collection beam within a fiber-optic probe head to collect Raman spectra. The invention may include optical elements to create the collimated collection beam if not already present or not suitable for insertion of the filter. A second "opaque" or neutral density filter may be insertable into the collimated collection beam to attenuate a broad spectral response within and outside the spectral range.

A method of dynamic range balancing in an optical spectrograph having a collimated collection beam includes the step of inserting a filter into the collimated collection beam to attenuate a predetermined spectral range characterized in having multi-component peaks of varying magnitude.

BRIEF DESCRIPTION OF THE DRAWINGS

FIG. 4A lists preferred filter edge recommendations corresponding to an excitation laser wavelength of 532 nm;

DETAILED DESCRIPTION OF THE INVENTION

Figure 1:
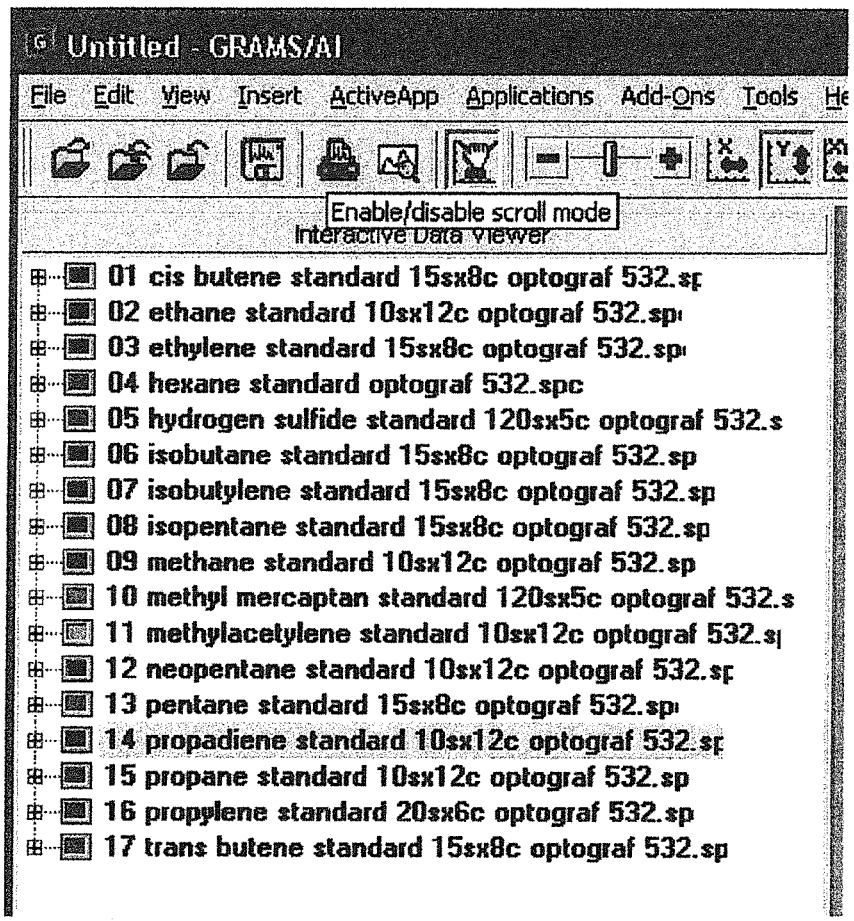
FIG. 1 is a table listing many different components identified in many hydrocarbon applications of Raman spectroscopy.
Figure 2:
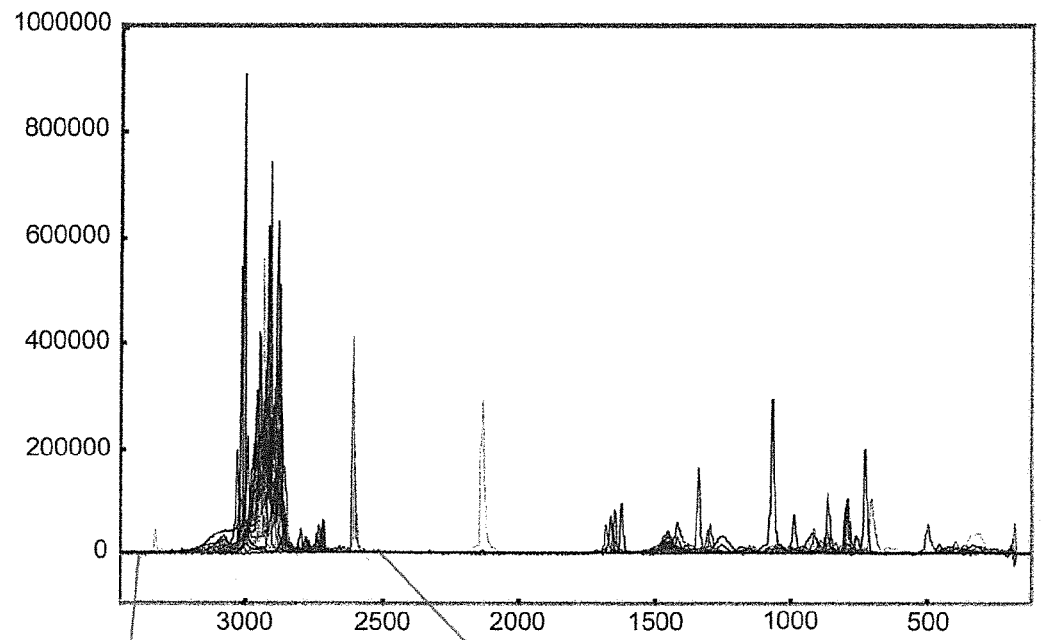
FIG. 2 is an overlay of pure gas signals representing the component gasses of interest in a typical hydrocarbon application.
Figure 3:
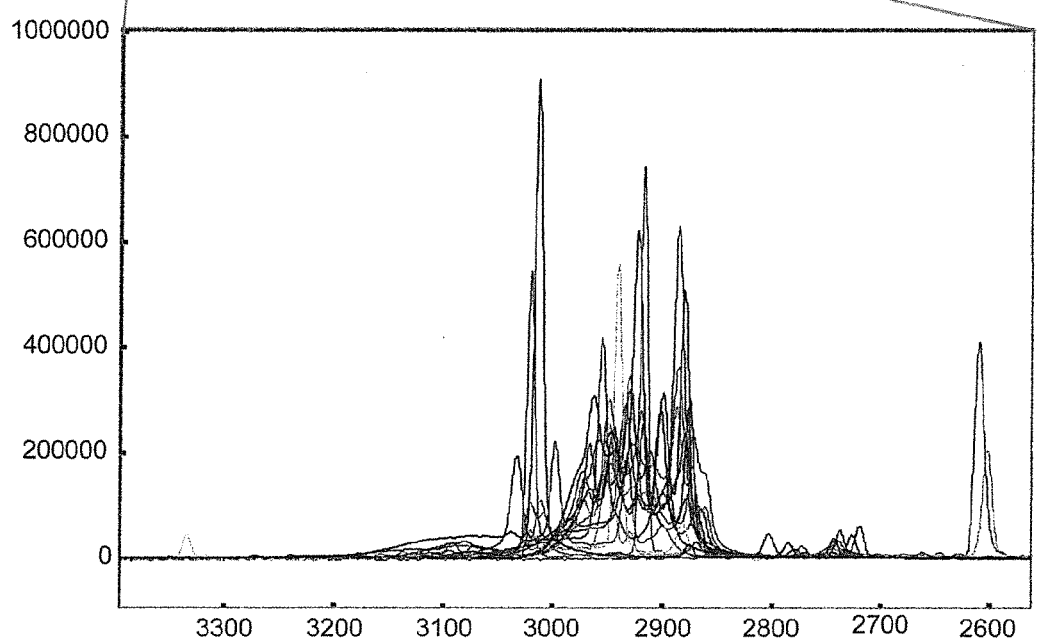
FIG. 3 is a detailed graph of a 'C—H stretch' region.
Figure 4B:
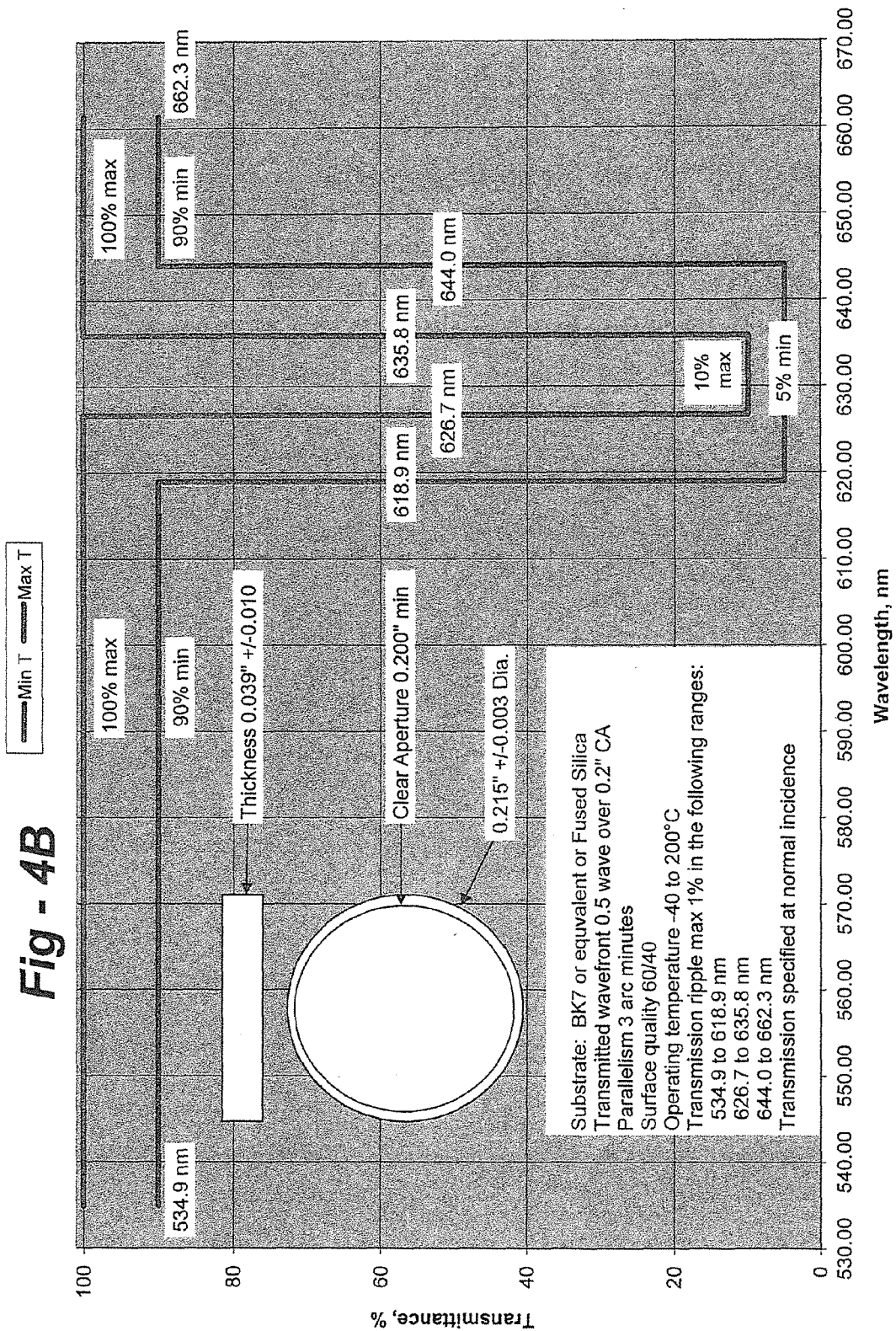
FIG. 4B provides the characteristics of a particular attenuation filter corresponding to an excitation laser wavelength of 532 nm.

This invention resides in methods and apparatus for dynamic range balancing for multi-component peaks of widely varying magnitude in an optical spectrometer. The preferred embodiment is directed to filters that attenuate the C—H stretch region to produce a better fit of a multi-component hydrocarbon Raman spectrum to the dynamic range of a CCD detector. Variants for dynamic range balancing in other applications will be apparent to those of skill in the art. In the preferred embodiment, the filter edge characteristics are specified as shown in FIGS. 4A and 4B, where the filter notch position in wavelength space corresponds to Raman scattering in the C—H stretch region under 532 nm laser excitation. The filter may be rigidly installed in any collimated collection path or adjustably positioned in or out of the collimated collection beam as described below.

Figure 5:
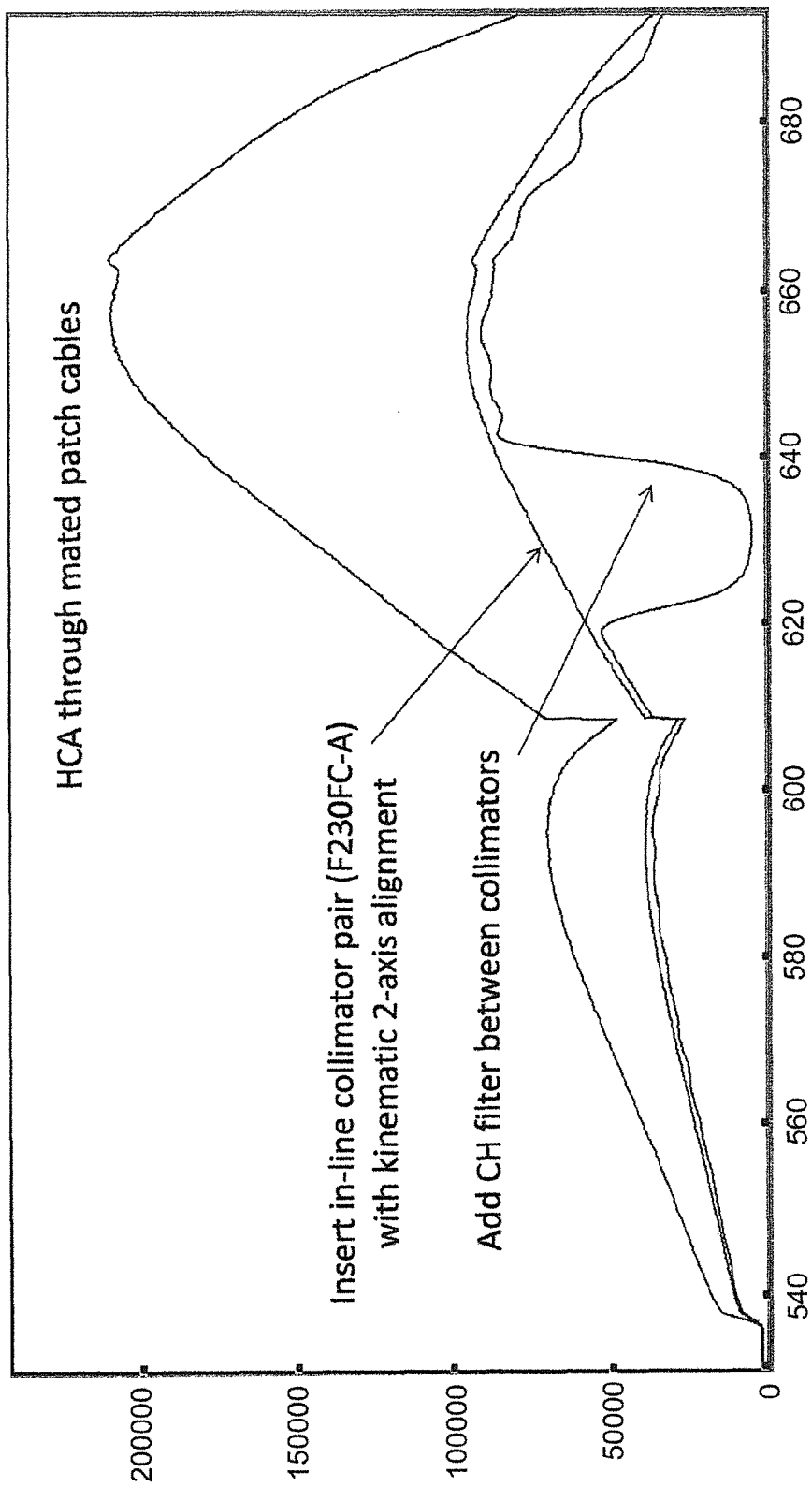
FIG. 5 is a graph of an in-line fiber C—H filter showing the degree of attenuation of a tungsten halogen lamp spectrum between about 620 and 640 nm.
Figure 6:
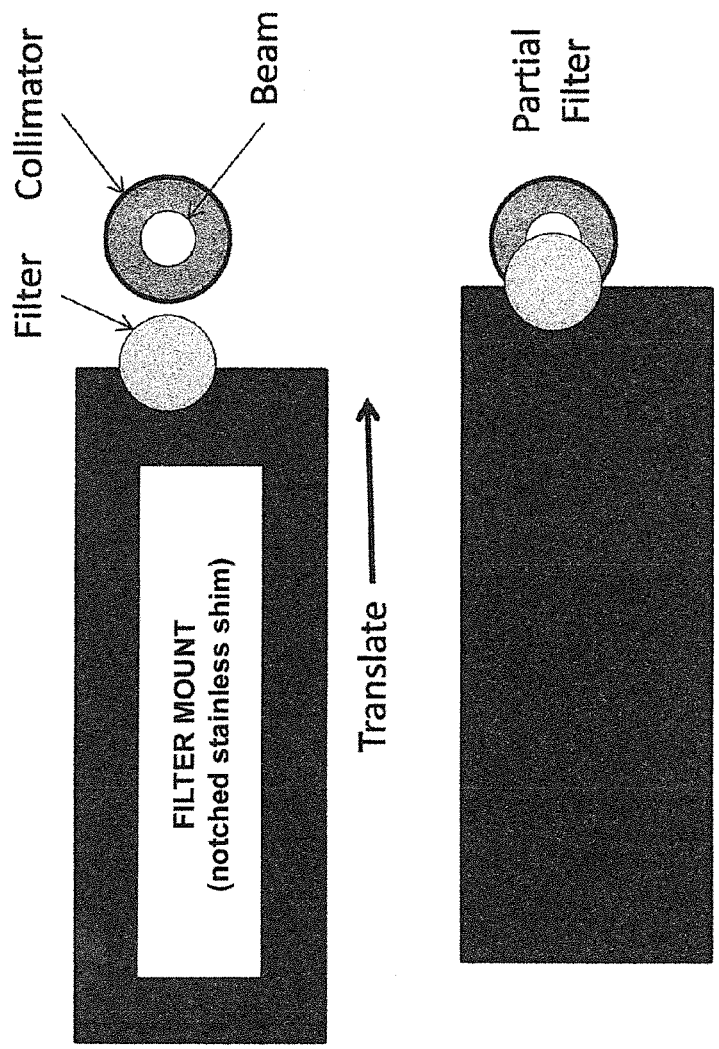
FIG. 6 is a simplified diagram depicting the way in which a filter may be mounted relative to the collimated beam to provide variable degrees of attenuation.
Figure 7:
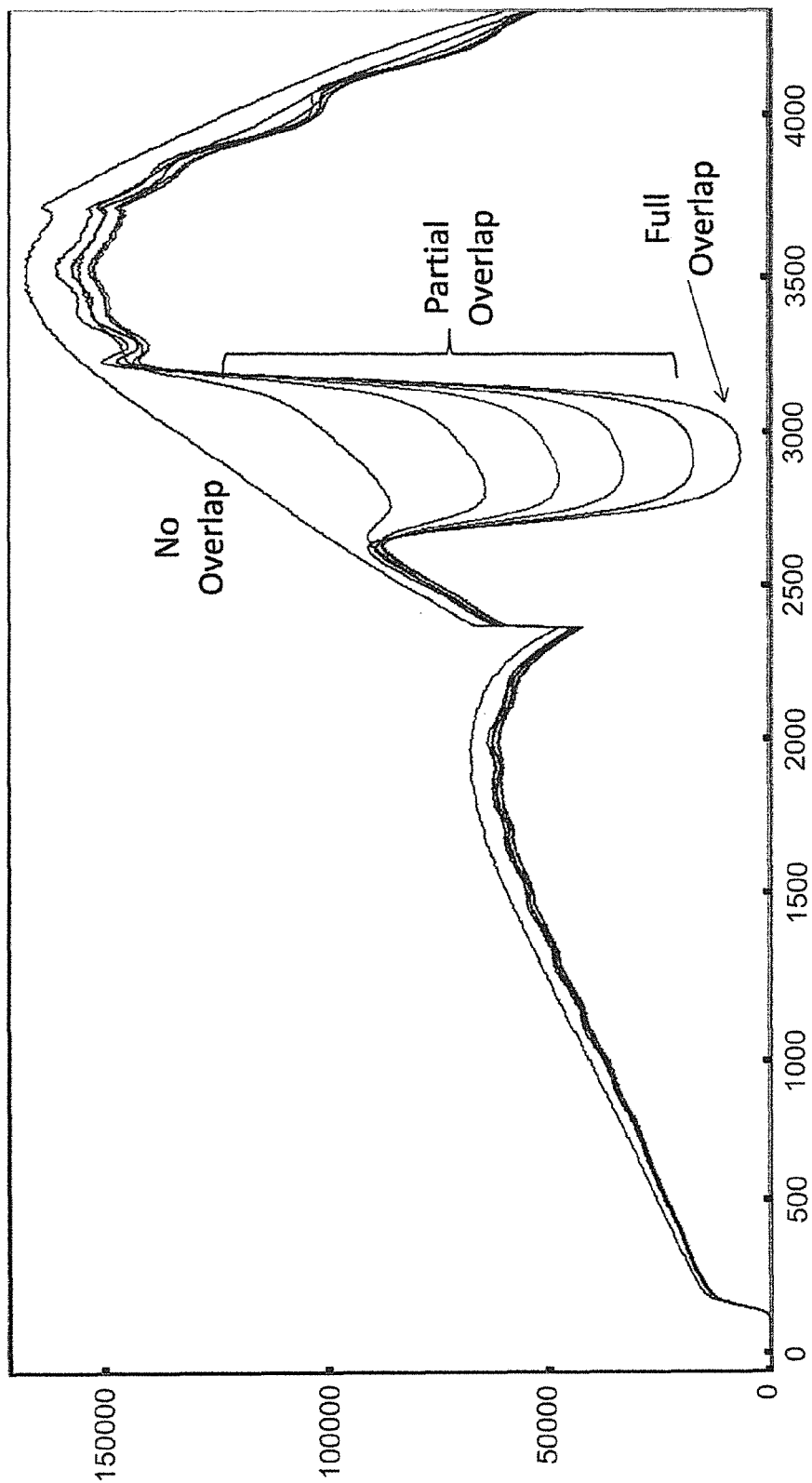
FIG. 7 shows how a tungsten halogen lamp spectrum is affected through stages of translation of the filter of FIG. 6.
Figure 8:
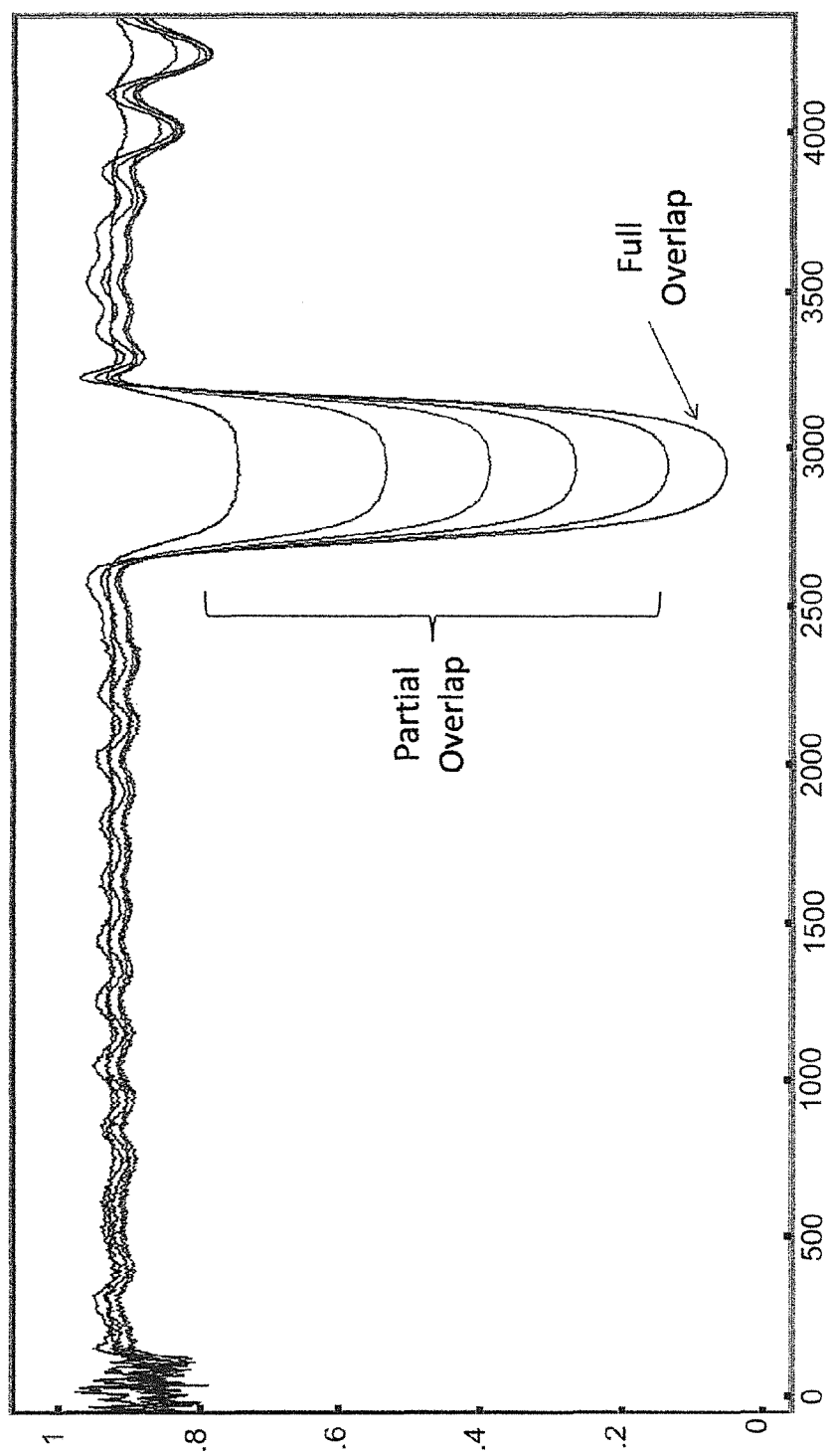
FIG. 8 depicts the transmittance of the filter itself from no overlap to full overlap.

FIG. 5 is a graph of an in-line fiber C—H filter showing the degree of attenuation of a tungsten halogen lamp spectrum between about 620 and 640 nm. This corresponds to the C—H stretch region for a Raman spectrum excited by a laser wavelength of 532 nm. FIG. 6 is a simplified diagram depicting the way in which a filter may be mounted relative to the collimated beam to provide variable degrees of attenuation. FIG. 7 shows how a tungsten halogen lamp spectrum is affected through stages of translation of the filter of FIG. 6. FIG. 8 depicts the transmittance of the filter itself from no overlap to full overlap.

Figure 9:
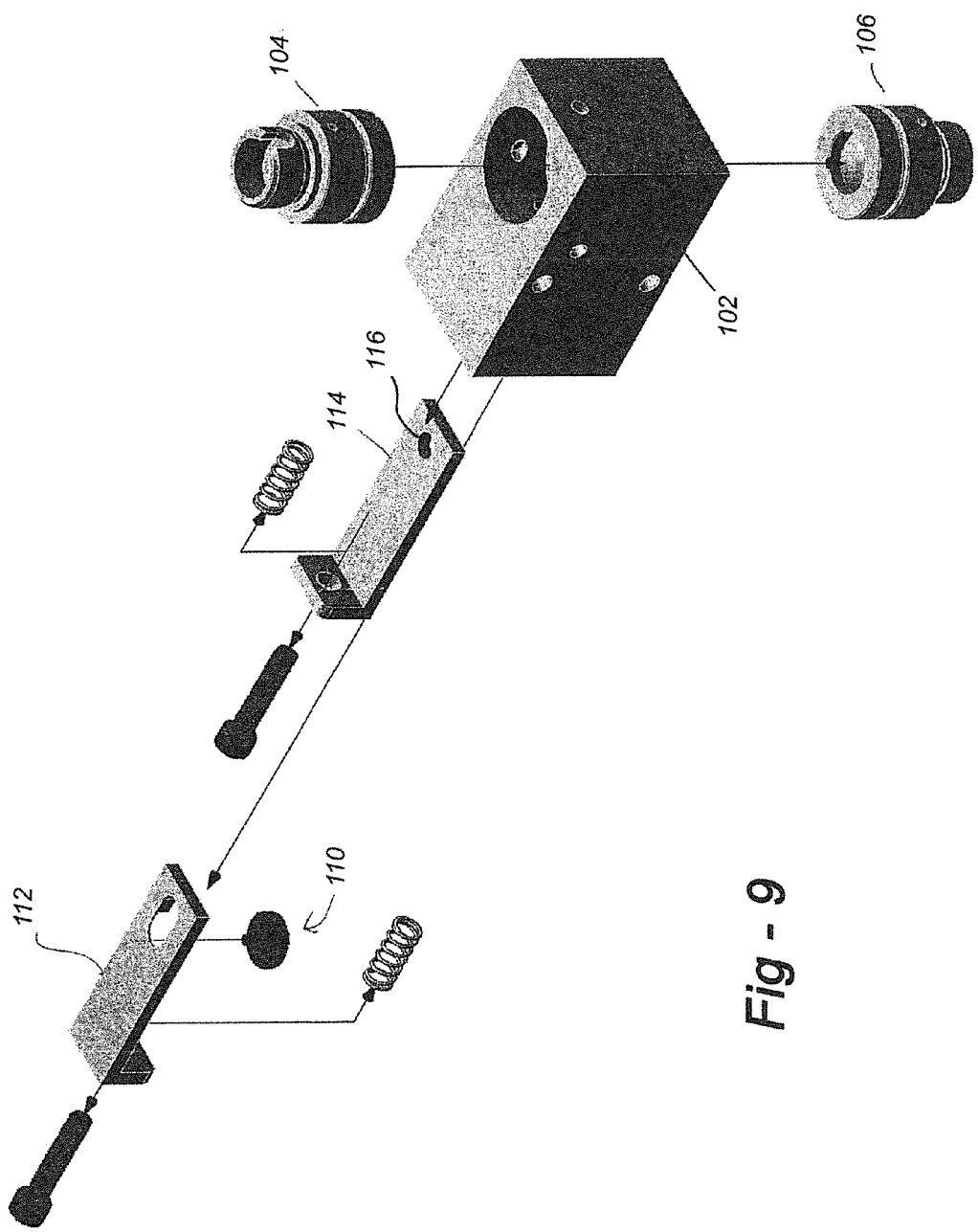
FIG. 9 is an exploded view of an accessory that may be used with existing systems, including fiber-based systems, to attenuate and/or block spectral ranges.

FIG. 9 is an exploded view of an accessory that may be used with existing systems, including fiber-based systems, to attenuate and/or block spectral ranges. The apparatus includes a housing to which collimators 104, 106 are mounted to provide a collimated beam within the housing. The spectral range attenuation filter 110 is mounted to a first slider 112, while an optional second slider 114 may be used to provide spectrally neutral attenuation via a sliding aperture 116. The springs are used as an opposing force to the adjustment screws. As an alternative to manual operation, either or both of the sliders 112, 114 may be motor or actuator driven, with positioning being a function of external inputs such as sample stream intensity.

Figure 10:
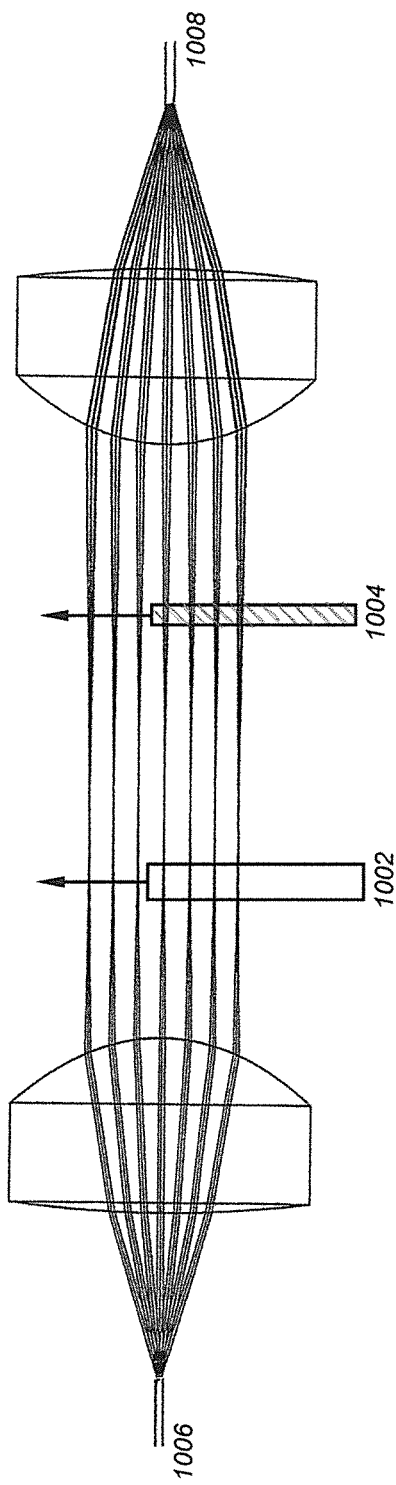
FIG. 10 is a cross section illustrating how a C—H spectral range filter and neutral "opaque" aperture filter may be moved in and out of the collimated path between input and output fibers.

FIG. 10 is a cross section illustrating how the C—H spectral range filter 1002 and neutral "opaque" aperture filter 1004 may be moved in and out of the collimated path between input and output fibers 1006, 1008. The C—H filter in this case is moved in and out to vary C—H notch depth, for example, whereas the opaque aperture stop may be moved in and out to attenuate the full spectrum for channel balancing in a multi-channel analyzer. The aperture filter may be alternatively replaced with a fully inserted fixed neutral density filter if adjustability is not required.

Figure 11:
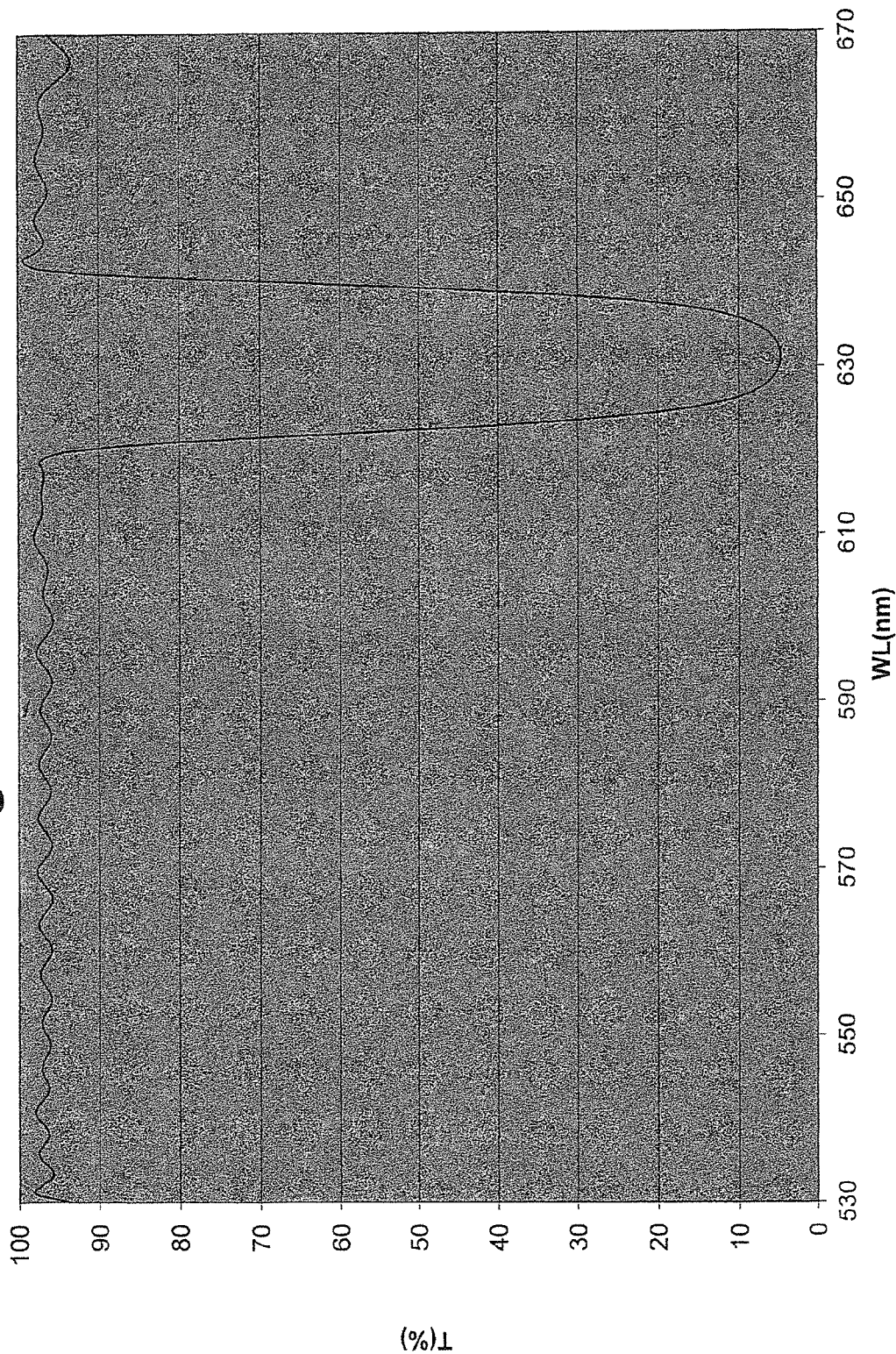
FIG. 11 illustrates the as-manufactured transmission characteristics of a multi-layer dielectric notch filter applicable to the invention, which was designed to the specifications of FIG. 4.

FIG. 11 illustrates the as-manufactured transmission characteristics of a multi-layer dielectric notch filter applicable to the invention, which was designed to the specifications of FIG. 4.

Figure 12:
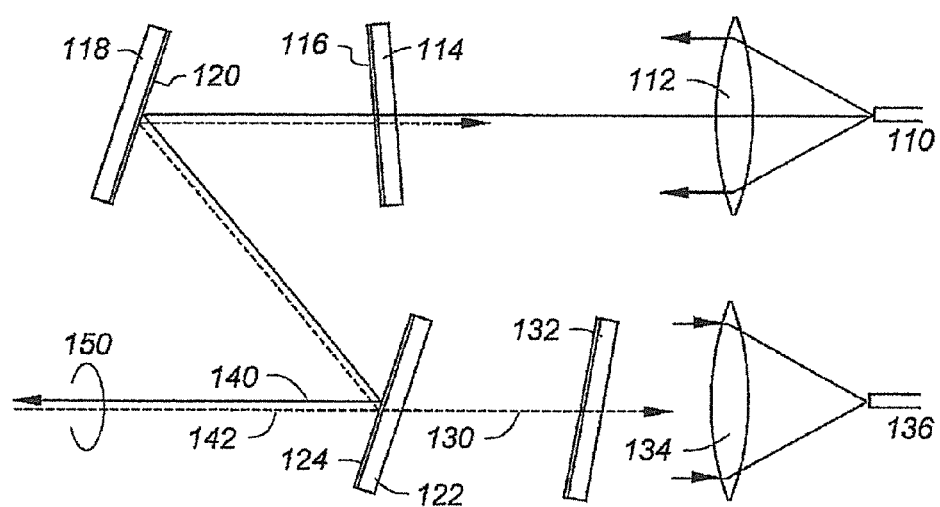
FIG. 12 is a diagram of a probe-head section applicable to the invention.
Figure 13:
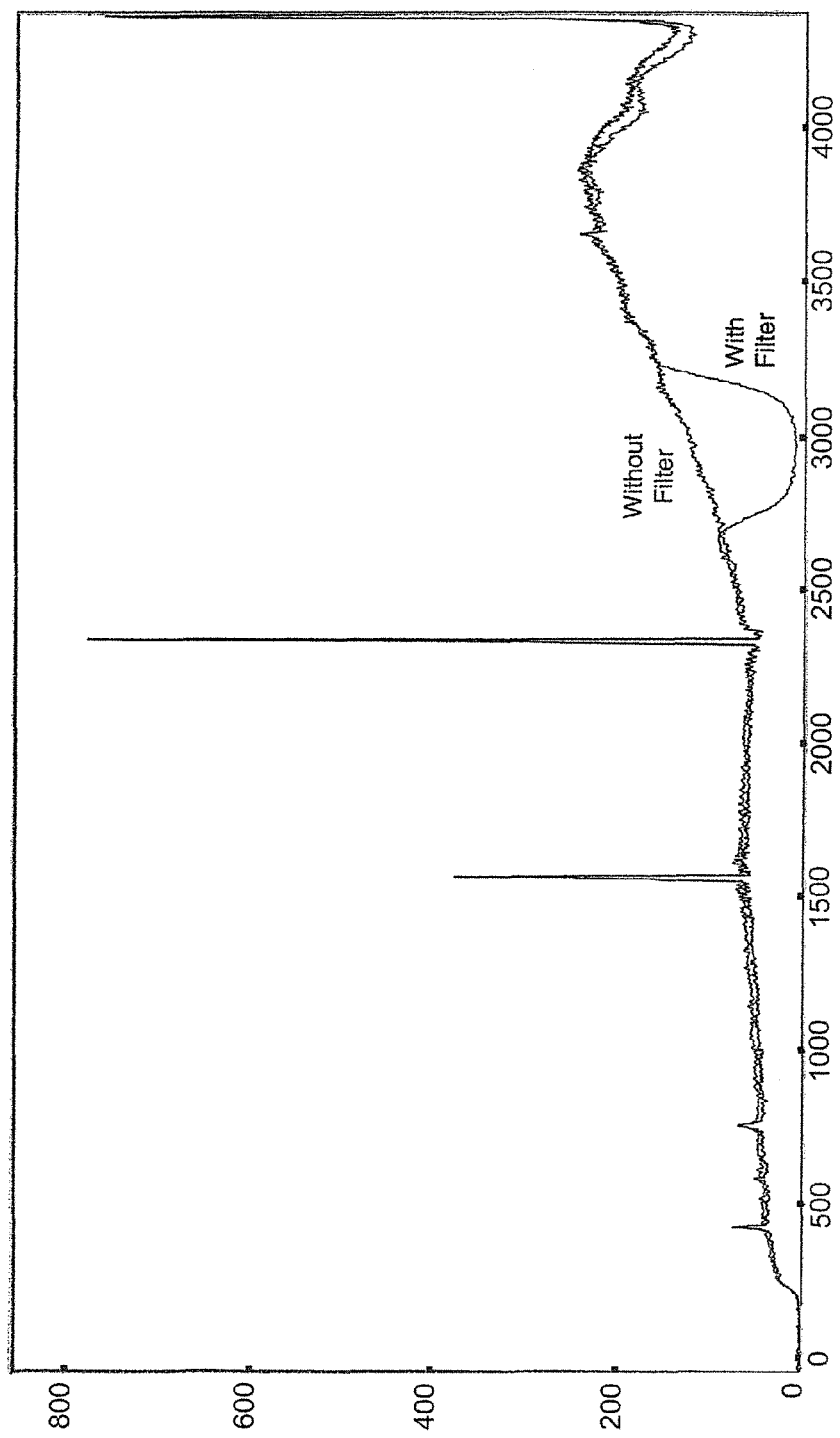
FIG. 13 is a graph showing a C—H stretch filter installed in a fiber-based probe head.

As an alternative to the drop-in assembly of FIG. 9, the filter(s) of the invention may be positioned within the collimated space of the spectrograph itself or added to a probe head if a collimated collection beam is available. FIG. 12 is a diagram of a probe-head section applicable to the invention. Laser light from excitation fiber 110 is collimated by lens 112 and bandpass filtered by coating 116 on substrate 114. A fold mirror coating on substrate 118 redirects the light onto combiner coating 124 on substrate 122, which forms co-propagating beam 150 containing excitation beam 140 and Raman collection signal 142. The collection signal passes through combiner 124, 122 as beam 130, which is notch filtered by element 132 and focused by lens 134 onto the input of collection fiber 136. Thus, in this configuration, the C—H or other range attenuation filter may be positioned in the space between the combiner and the lens 134. The filter(s) may either be permanently installed in the beam 130 or slid in and out manually or automatically based upon sample stream intensity. FIG. 13 is a graph showing a C—H stretch filter installed in a fiber-based probe head.

The invention claimed is:

1. In an optical spectrograph having a sensor with a dynamic range configured to receive a collimated collection beam with a Raman spectra including weak signals of interest and strong, multi-component peaks of varying magnitude, the improvement comprising:
   a filter, insertable into the collimated collection beam to attenuate a predetermined range within the Raman spectra including the strong multi-component peaks, thereby improving the signal-to-noise ratio (SNR) of the weak signals and balancing the weak and strong signals relative to the dynamic range of the sensor.

2. The improvement of claim 1, wherein the filter is translatable into and out of the collimated collection beam to achieve a varying degree of attenuation within the spectral range.

3. The improvement of claim 1, wherein the filter is insertable into a collimated collection beam within a fiber-optic probe head to collect the Raman spectra.

4. The improvement of claim 1, further including optical elements to create the collimated collection beam for insertion of the filter.

5. The improvement of claim 1, wherein the strong signals correspond to a C—H stretching region.

6. The improvement of claim 1, further including an opaque or neutral density filter insertable into the collimated collection beam to uniformly attenuate the Raman spectra including both the strong and the weak signals.

7. A method of dynamic range balancing in an optical spectrograph having a collimated collection beam with a Raman spectra including weak signals of interest and strong, multi-component peaks of varying magnitude, the method comprising the step of:

inserting a filter into the collimated collection beam to attenuate a predetermined range within the Raman spectra including the strong, multi-component peaks, thereby improving the signal-to-noise ratio (SNR) of the weak signals relative to the strong signals.

8. The method of claim 7, including the step of translating the filter into and out of the collimated collection beam to achieve a varying degree of attenuation.

9. The method of claim 7, including the step of translating the filter into and out of a collimated collection beam within a fiber-optic probe head to collect the Raman spectra.

10. The method of claim 7, including the step of creating the collimated collection beam with lenses or other optical components.

11. The method of claim 7, wherein the strong signals correspond to a C—H stretching region.

12. The method of claim 7, including the step of inserting an opaque or neutral density filter into the collimated collection beam to uniformly attenuate the Raman spectra including both the strong and the weak signals.

\* \* \* \* \*